United States Patent [19]

Zaiger et al.

[11] Patent Number: Plant 5,831

[45] Date of Patent: Dec. 16, 1986

[54] PEACH TREE ("ZEE-RED")

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 698,122

[22] Filed: Feb. 4, 1985

[51] Int. Cl.[4] ..... A01H 5/03

[52] U.S. Cl. ..... Plt./43

[58] Field of Search ..... Plt./43

*Primary Examiner*—Robert E. Bagwill

[57] ABSTRACT

This new and distinct variety relates to a peach tree which has the following unique combination of desirable features:

1. Relatively uniform size of fruit throughout the tree.
2. Fruit with attractive red skin color.
3. Heavy and regular fruit production.
4. Fruit with very firm flesh and very good storage and shipping quality.
5. Vigorous, upright growth.
6. Fruit with good flavor and eating quality.

1 Drawing Figure

ORIGIN OF THE VARIETY

The present variety of peach tree was originated by us in the experimental orchard located at Modesto, Calif., as a first generation seedling from a cross between Fayette Peach (Non-patented) and May Red Nectarine (U.S. Plant Pat. No. 2,758). A large group of seedlings from this cross were grown and maintained under careful observation, during which time we recognized the desirable characteristics described above and selected the present variety for reproduction and commercialization.

ASEXUAL REPRODUCTION OF THE VARIETY

The present variety of peach tree was asexually reproduced by budding at the experimental orchard located at Modesto, Calif. and the reproductions show that all characteristics run true to form and are transmitted through succeeding propagations.

SUMMARY OF THE VARIETY

A new and distinct variety of peach tree which is of large size, medium dense, upright in growth and a regular and productive bearer of large, very firm, yellow flesh, freestone fruit characterized as to novelty by being nearly uniform in size throughout the tree, having attractive red skin color, being very firm flesh with good eating, storage and shipping quality and maturing 7 to 10 days before Fayette Peach (Non-patented).

DESCRIPTION OF THE PHOTOGRAPHS

The accompanying color photographs show typical specimens of the fruit and foliage of our new variety, with the upper and lower surface of the leaves being illustrated and the exterior and a cross sectional view of the fruit divided in its suture plane to reveal flesh coloration, and showing a stone remaining in place. The illustrations were taken shortly after being picked at maturity (shipping ripe) and the colors are as nearly true as is reasonably possible in color representations of this type.

DESCRIPTION OF THE VARIETY

The following is a botanical description of our new variety of peach tree, its foliage and fruit as based on observations of specimens grown at Modesto, Calif., with color terminology (except those in common terms)

in accordance with Reinhold Color Atlas by A. Kornerup and J. H. Wanscher.

Tree:
- *Size.*—Large.
- *Vigor.*—Vigorous.
- *Density.*—Medium dense.
- *Form.*—Upright.
- *Production.*—Productive.
- *Bearing.*—Regular.

Trunk:
- *Size.*—Medium to large.
- *Surface.*—Medium shaggy.
- *Color.*—Brownish gray.

Branches:
- *Size.*—Medium stocky.
- *Surface.*—Smooth to medium rough.
- *Lenticels.*—Medium number. Medium size.
- *Color.*—Brown to grayish brown.

Leaves:
- *Size.*—Large. Average length — 6". Average width — 1¾".
- *Form.*—Lanceolate. Tip acuminate.
- *Margin.*—Crenate.
- *Texture.*—Smooth.
- *Petiole.*—Average length — ¾". Average thickness — 3/32".
- Glands.—Reniform. Number varies 2 to 6. Average number 2. Positioned on base of leaf blade and upper part of petiole.
- *Color.*—Upper surface — green to dark green (28-E-8 to 28-F-8). Lower surface — grayish green to dull green (27-E-5 to 28-E-6).

Flower Buds:
- *Size.*—Large.
- *Length.*—Medium.

Flowers:
- *Blooming period.*—First bloom — Mar. 2, 1982. Full bloom — Mar. 6, 1982. Varies slightly with climatic conditions.
- *Size.*—Large — showy.
- *Pollen.*—Present.
- *Color.*—Pink.

Fruit:
- *Maturity when described.*—Hard ripe.

*Date of first picking.*—July 19, 1982.
*Date of last picking.*—July 24, 1982.
*Size.*—Large. Average diameter axially — 3". Average transversely in suture plane — 3".
*Form.*—Nearly globose, some fruit slightly larger on one side and slightly flattened at stem end.
*Suture.*—Usually shallow, extends from base to apex, with slight depression at pistil point.
*Ventral surface.*—Usually rounded, varies from equal to unequal.
*Cavity.*—Moderately rounded, slightly elongated in suture plane. Average depth — ½". Average breadth — ¾".
*Base.*—Retuse.
*Apex.*—Usually retuse, some fruit rounded.

Skin:
*Thickness.*—Medium.
*Texture.*—Medium, tenacious to flesh.
*Tendency to crack.*—None.
*Down.*—Moderate. Medium to short in length.
*Color.*—Bright yellow ground color (4-A-6 to 4-A-8) with red blush (8-A-7 to 9-A-7).

Flesh:
*Texture.*—Very firm.
*Fibers.*—Moderate to few — tender.
*Juice.*—Moderate.
*Amygdalin.*—Undetected.
*Ripens.*—Uniform, only slightly earlier at apex.
*Flavor.*—Mild.
*Aroma.*—Distinct.
*Eating quality.*—Good.
*Color.*—Butter yellow (4-A-5) to sunflower yellow (4-A-7). Stone cavity — red (9-A-6 to 9-A-8).

Stone:
*Type.*—Freestone.
*Size.*—Medium to large. Average length — 1½". Average width — 1¼". Average breadth — ¾".
*Form.*—Ovid.
*Sides.*—Mostly equal.
*Apex.*—Usually rounded — some acuminate.
*Base.*—Straight.
*Surface.*—Irregularly furrowed toward apex.
*Ridges.*—Rounded.
*Tendency to split.*—Very slight.
*Color.*—Light brown to reddish brown.

Use: Dessert.
*Market.*—Local and long distance.
Keeping Quality: Very good.
Shipping quality: very good.

The peach tree and its fruit herein described may vary in slight detail due to climatic, soil and cultural practices under which the variety may be grown. The description above is that of the variety produced under the ecological conditions prevailing at Modesto, Calif.

The following is claimed:

1. A new and distinct variety of peach tree, as illustrated and described, characterized by its large size, vigorous, upright growth and being a productive and regular bearer of large, very firm, yellow flesh, freestone fruit with good eating, storage and shipping quality; the fruit is further characterized by being relatively uniform in size throughout the tree, having an attractive red skin color, and maturing 7 to 10 days before Fayette Peach (Non-patent).

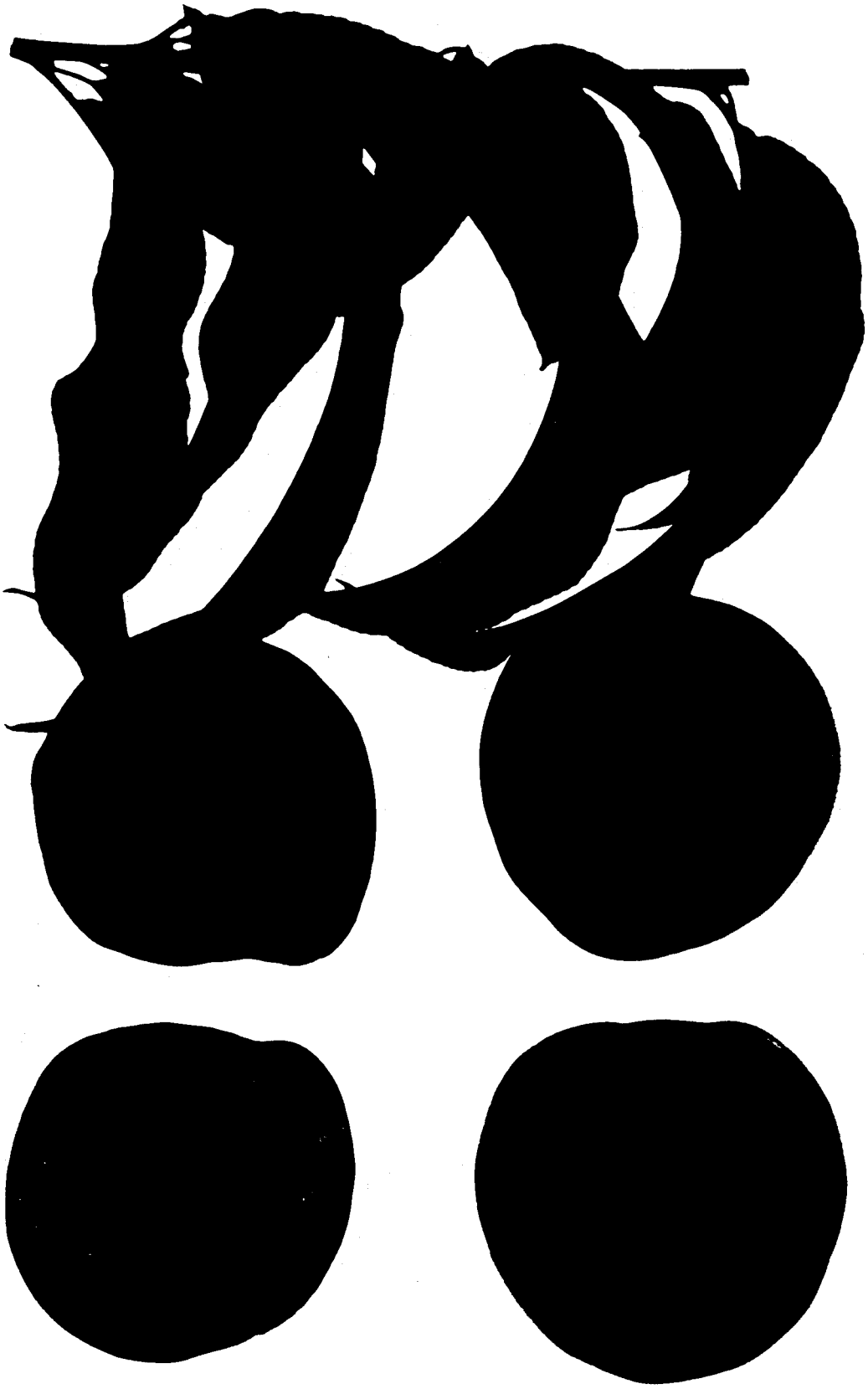

* * * * *